United States Patent [19]

Tamura

[11] Patent Number: 4,832,839

[45] Date of Patent: May 23, 1989

[54] HEMOPURIFICATION APPARATUS

[75] Inventor: Makio Tamura, Matsudo, Japan

[73] Assignee: Japan Organo Co., Ltd., Tokyo, Japan

[21] Appl. No.: 96,799

[22] Filed: Sep. 15, 1987

Related U.S. Application Data

[63] Continuation of Ser. No. 844,971, Mar. 27, 1986, abandoned.

[30] Foreign Application Priority Data

Mar. 29, 1985 [JP] Japan .................................. 60-063744

[51] Int. Cl.$^4$ .............................................. B01D 19/00
[52] U.S. Cl. ..................................... 210/188; 210/295; 210/321.75; 210/340
[58] Field of Search ............... 210/188, 259, 266, 295, 210/321.84, 321.61, 321.75, 640, 641, 340; 422/45, 46, 48; 424/101

[56] References Cited

U.S. PATENT DOCUMENTS

| | | | |
|---|---|---|---|
| 3,651,616 | 3/1972 | Blanchard et al. | 210/640 |
| 4,218,321 | 8/1980 | Sasaki et al. | 210/321.3 |
| 4,311,594 | 1/1982 | Perry | 210/640 |
| 4,411,786 | 10/1983 | Russell | 210/321.4 |
| 4,568,327 | 2/1986 | Seufert | 210/646 |

OTHER PUBLICATIONS

Chang, T. M. S., "Hemoperfusion Alone and in Series with Ultrafiltration or Dialysis for Uremia, Poisoning and Liver Failure", Kidney International, vol. 10, Oct., 1976, pp. S-305-S-311.

Primary Examiner—Richard V. Fisher
Assistant Examiner—Coreen Y. Lee
Attorney, Agent, or Firm—Oblon, Fisher, Spivak, McClelland & Maier

[57] ABSTRACT

A hemopurification apparatus includes a porous membrane permeable to gas but impermeable to liquid and dividing a container into two mutually-isolated compartments. The apparatus is adapted to remove water from blood by causing the blood to flow through one of the compartments and a fluid, the water vapor pressure of which is lower than that of the blood, to flow through the other compartment, whereby a portion of the water in the blood is allowed to pass as water vapor through the porous membrane.

2 Claims, 3 Drawing Sheets

HEMOPURIFICATION APPARATUS

This application is a continuation of application Ser. No. 06/844,971, filed on Mar. 27, 1986, now abandoned.

BACKGROUND OF THE INVENTION

1. Field of the Invention

The present invention relates to a hemopurification apparatus, and more specifically to a hemopurification apparatus which permits removal of water from blood without loss of effective and useful constituents from the blood upon dialytic therapy of patients with chronic renal failure or heart diseases, enables more sophisticated hemopurification therapy through its combined use with a conventional hemodialyzer or the like, and materializes, by itself or through its combination with an adsorbent or the like, both size and weight reduction to such a significant extent that the apparatus is portable.

2. Description of the Prior Art

Conventional hemopurification methods include hemodialysis, hemofiltration, direct hemoperfusion, etc.

In hemodialysis, blood is caused to flow through one of two compartments divided from each other by means of a dialytic, i.e., semipermeable membrane such as regenerated cellulose or polyacrylonitrile while a dialysate is caused to flow through the other compartment. Waste metabolites in the blood, for example, urea, uric acid, creatinine, electrolytes and the like are removed owing to the difference in concentration between the blood and the dialysate and at the same time, a pressure is applied to the blood to remove water from the blood owing to the difference in pressure between the blood and the dialysate.

In hemofiltration, blood is caused to flow through one of two compartments divided from each other by means of an ultrafiltration membrane. By applying a pressure to the blood, waste metabolites in the blood, for example, urea, uric acid, creatinine, electrolytes, water and the like are removed, primarily, by filtration.

In direct hemoperfusion, an activated carbon adsorbent, high molecular adsorbent or the like is brought into contact with blood either as is or after coating such an adsorbent with a material having good biocompatibility with blood, so that Waste metabolites in the blood, for example, urea, uric acid, creatinine and the like are adsorbed and hence removed.

The above-described conventional hemopurification methods are however accompanied by the following drawbacks.

In order to remove water from blood by hemodialysis, filtration is effected by using a dialytic membrane in much the same way as an ultrafiltration membrane. The method however allows electrolytes and useful constituents to flow out along with water from the blood. When hemodialysis is performed, urea, uric acid and the like are also removed from the blood and the osmotic pressure of the blood is hence lowered significantly to such a level that it becomes lower than the osmotic pressure of body fluids contained in cells of the body. As a result, water is caused to penetrate from the blood into the cells and although water must also be removed from the cells for successful hemodialysis, the water contents in the cells increase conversely. In order to avoid such osmotic pressure reduction in blood, it is now practiced to increase the concentration of Na+ ions in a dialysate so as to increase the concentration of Na+ ions in blood. This approach is however not believed to be the best method for patients, because Na+ ions which are supposed to be removed from blood for successful dialysis are increased conversely. Further, hemodialysis requires a great deal of dialysate in order to maintain a suitable difference in concentration between the dialysate and blood. A dialysate as much as about 100 l is generally required for dialytic therapy of 5 hours. Corollary to this, it is difficult to reduce the dimensions and weight of the purification apparatus of a hemodialysis system.

In hemofiltration, useful constituents, electrolytes and the like are also caused to flow out, along with waste metabolites, for instance, urea, uric acid, creatinine, water, middle molecules (hereinafter abbreviated "M.M." for the sake of brevity) and the like, from the body into a filtrate separated from blood. Moreover, the filtrate has to be produced in a large volume in order to achieve sufficient removal of waste metabolites from blood. As a result, the water level in the blood is reduced excessively. It is hence necessary to replenish the thus-lost electrolytes, useful constituents and water after the hemofiltration but before putting the thus-filtered blood back into the body. This replenishment is called "replacement fluid". In general, about 20 l of replacement fluid is required for single hemofiltration therapy. Since this replacement fluid is put directly into the body, it must be very clean. Here again, it is difficult to reduce the dimensions and weight of the purification apparatus of a hemofiltration system.

Direct hemoperfusion is effective for the removal of waste metabolites in blood, for example, urea, uric acid, creatinine, M.M., etc. Its apparatus may be fabricated into a compact structure. Direct hemoperfusion is however unable to remove water from blood.

SUMMARY OF THE INVENTION

An object of this invention is to provide a hemopurification apparatus which can remove only water from blood without losing effective constituents in the blood, although this has been impossible to achieve by any conventional apparatus.

Another object of this invention is to provide a hemopurification apparatus which can be fabricated into a smaller and lighter structure.

A further object of this invention is to provide a hemopurification apparatus which enables more sophisticated hemopurification therapy through its combined use with a conventional hemodialyzer or the like.

In one aspect of this invention, there is thus provided a hemopurification apparatus comprising a porous membrane permeable to gas but impermeable to liquid and dividing a container into two mutually-isolated compartments. The apparatus being adapted to remove water from blood by causing the blood to flow through one of the compartments and a fluid, the water vapor pressure of which is lower than that of the blood, to flow through the other compartment, whereby a portion of the water in the blood is allowed to pass as water vapor through the porous membrane.

Since substances other than water is not removed by the apparatus of this invention, the osmotic pressure of blood can be easily increased unlike conventional hemodialysis in which the osmotic pressure of blood is lowered significantly. As a result, the osmotic pressure of the blood becomes higher than that of the fluids in cells of the body and the transfer of water from the cells into the blood, which has been difficult to achieve by any conventional hemodialysis, is facilitated. More efficient hemopurification therapy can also be applied by making use of the above-mentioned advantageous features of the apparatus of this invention and combining it with a conventional hemopurification apparatus. Since the hemopurification apparatus of this invention is more suited for size and weight reduction than those employed to practice conventional hemodialysis or hemofiltration, the apparatus for a hemopurification system can be reduced in both dimensions and weight by using the hemopurification apparatus of this invention either alone or in combination with an apparatus for practicing direct hemoperfusion and the like, whereby hemofiltration therapy has now been rendered available at home and at work and in addition, development of a wearable apparatus for a hemopurification system has now been rendered feasible.

The above and other objects, features and advantages of this invention will become apparent from the following description and the appended drawings, taken in conjunction with the accompanying drawings.

DETAILED DESCRIPTION OF THE INVENTION AND PREFERRED EMBODIMENTS

Figure 1:
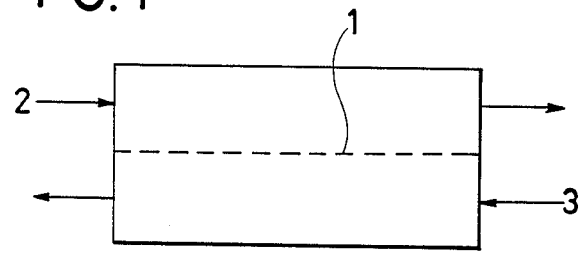
FIGS. 1 and 2 illustrate the principle of the hemopurification apparatus according to this invention.
Figure 2:
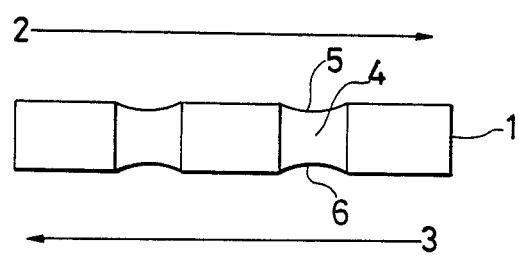

The principle of this invention is illustrated in FIGS. 1 and 2.

Blood 2 is caused to flow through one of two compartments which are divided from each other by means of a porous membrane 1 permeable to gas but impermeable to liquid, while a fluid 3 having a water vapor pressure lower than that of the blood is caused to flow through the other compartment. The porous membrane 1 does not permit passage of any liquid therethrough and contains a number of pores 4 which do not contain any liquid therein. Water vapor, which has emanated from the blood 2 at each opening 5 on the membrane surface and then entered the corresponding pore 4, is absorbed through an opening 6 on the opposite membrane surface in the fluid 3 if the fluid 3 is a liquid. If the fluid 3 is a gas, the water vapor is absorbed in the stream of the gas by a similar mechanism.

The porous membrane 1 useful in the practice of this invention will next be described. Any material may be used as the porous membrane 1 so long as it is a membrane permeable to gas but impermeable to liquid. For this purpose, it is preferred to use a hydrophobic material such as polytetrafluoroethylene, polypropylene or polyethylene. Although it may take any shape including a planar membrane, hollow fibers and the like, a hollow fiber form featuring a large effective surface area is desirable. The thinner the membrane thickness, the greater the permeation rate of water vapor and the more desirable the membrane, so long as its strength is acceptable. The pore size of the porous membrane must be small enough to prevent passage of blood therethrough. Although subject to each membrane material and the pressure upon each application of the hemopurification apparatus, the possible maximum pore size may preferably range from 0.02 $\mu$m to 10 $\mu$m. Any pore sizes smaller than 0.02 $\mu$m tend to make passage of water vapor difficult. If the pore size exceeds 10 $\mu$m on the other hand, blood tends to leak out. It is therefore not preferred to employ any pore sizes outside the above-specified range. It is also desirable to make the porosity of the membrane as greater as possible, because the permeation rate of water vapor increases as the porosity becomes greater.

Incidentally, the pore sizes as mentioned above are those pore sizes which are specified in catalogs and the like issued by manufacturers of hydrophobic porous membranes.

The fluid 3 the water vapor pressure of which is lower than that of blood may be either liquid or gas. As exemplary liquids, may be mentioned deionized water, physiological saline and the like, each of which has a temperature lower than the blood 2. In view of the danger that the membrane could be damaged or ruptured, physiological saline is desired because it gives less influence even when mixed with blood. As the temperature of the liquid becomes lower, its water vapor pressure becomes lower with a resultant greater difference in the vapor pressure between the liquid and the blood, and as a result, the permeation rate of water vapor increases. If the temperature of the liquid is excessively low, the temperature of the blood 2 located on the opposite side relative to the porous membrane 1 is also lowered. Hence, some deleterious effects are given to blood constituents and the fluidity of the blood is reduced. It is therefore desirable to maintain the temperature of the liquid around room temperature (10° C.–38° C.). When a gas is employed as the fluid 3, the gas is not necessarily limited to any specific type so long as it is free of toxicity. Clean air or the like may hence be used by way of example. It is possible to accelerate the permeation of water vapor by reducing the pressure of the gas, for example, air.

Various modes of application of the hemopurification apparatus, all of which find their basis on the above-described principle, will next be described with reference to FIGS. 3 through 7.

Figure 3:
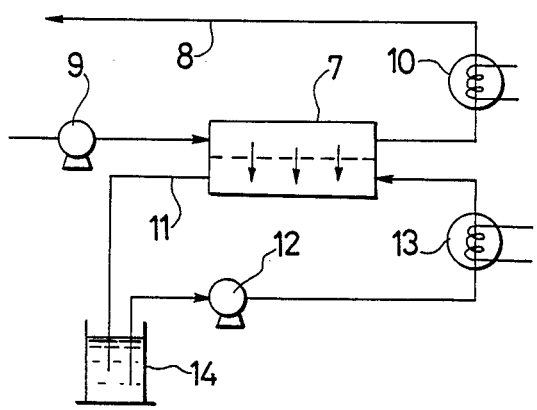
FIGS. 3 through 7 show different modes of application of the hemopurification apparatus.

FIG. 3 shows an example of the basic construction of this invention. Blood 8 is caused to flow by a blood pump 9 into one of two compartments of a hemopurification module 7 which has been constructed in accordance with this invention and makes use of a porous membrane. The blood 8 from which water has been removed in the hemopurification module 7 is adjusted in temperature at a heat exchanger 10 prior to its return into the body. On the other hand, an absorption liquid 11 (a liquid having a water vapor pressure lower than that of the blood 8) is caused to flow by an absorption liquid pump 12 from an absorption liquid tank 14, via a heat exchanger 13 for controlling the temperature of the absorption liquid, into the other compartment of the hemopurification module 7. The absorption liquid 11 which has absorbed water vapor from the blood 8 in the hemopurification module 7 returns to the absorption liquid tank 14. In the above construction, the blood pump 9 may be omitted provided that the blood 8 is allowed to flow by making use of the blood pressure. The absorption liquid tank 14 is not necessarily indispensable and the absorption liquid may be allowed to overflow from the absorption liquid flow line at the same rate as water is absorbed from the blood 8.

As mentioned above, the hemopurification system according to this invention may theoretically be able to remove water from blood by using the absorption liquid in a small amount. As the heat exchanger 13 which is employed to adjust the temperature of the absorption liquid 11, an air heat exchanger may be employed successfully. The hemopurification system of this invention can thus be reduced in both dimensions and weight, compared with conventional hemopurification systems.

Figure 4:
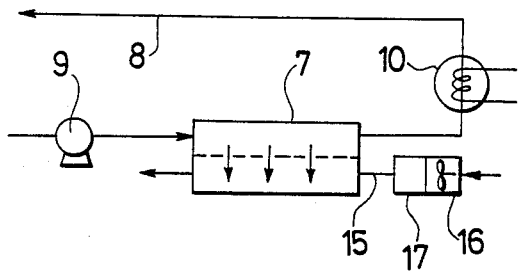

In FIG. 4, a gas having a water vapor pressure lower than that of blood, e.g., clean air 15 in the drawing is used in place of the absorption liquid 11 employed in the system of FIG. 3. Air is introduced by a blower 16 from the outside of the system. After passing through a gas filter 17, the air flows into a compartment opposite to the blood-flowing compartment of the hemopurification module 7 and absorbs water vapor. Thereafter, the air is exhausted out of the system. Since the pore size of the porous membrane used in the hemopurification module 7 is as small as 0.02–10 μm, the gas filter is not absolutely necessary. The air blower 16 may be provided either at the inlet side or at the outlet side of the hemopurification module 7. The system of FIG. 4 may be fabricated into a still smaller structure than the system of FIG. 3.

Figure 5:
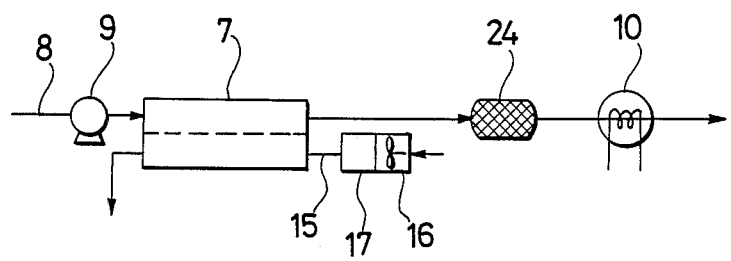

The system depicted in FIG. 5 includes a direct hemoperfusion module 24 in addition to the system of FIG. 4. The hemopurification module of this invention can remove only water from blood. In order to remove waste metabolites such as urea, uric acid, creatinine, M.M. and the like, a direct hemoperfusion module 24 is employed in combination. As an adsorbent, activated carbon, high molecular adsorbents, ion exchange resins and the like may be used either singly or in combination. The surface of the adsorbent may be coated with a substance having good compatibility with blood (for example, albumin). The system of FIG. 5 can remove both water and waste metabolites from blood and can be fabricated into a small structure. If the direct hemoperfusion module 24 is designed as a cartridge-type module so as to permit its replacement by a patient himself, hemopurification therapy can be effected at home and offices.

Figure 6:
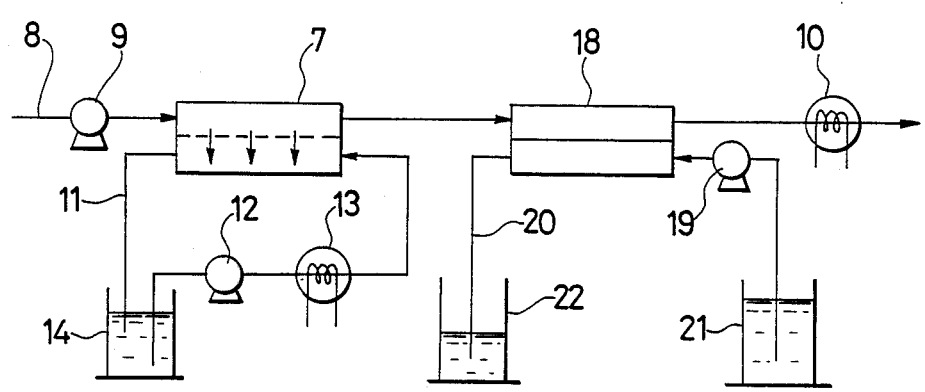

FIG. 6 shows a combined system of a hemopurification system of this invention and a conventional hemodialysis system. By tee blood pump 9, the blood 8 is caused to flow in the hemopurification system of this invention, which is similar to that illustrated in FIG. 3. Water is only removed from the blood 8 in the hemopurification module 7 of this invention. As a result, the concentrations of waste metabolites, i.e., urea, uric acid, creatinine, M.M. and the like in the blood increase. Thereafter, the blood 8 flows in the conventional hemopurification system. A dialysate 20 is caused to flow by a dialysate pump 19 from a dialysate reservoir 21 into a hemodialysis module 18, in which the dialysate 20 absorbs waste metabolites, for example, urea, uric acid, creatinine, M.M. and the like from the blood 8 and then flows into a dialysate receptacle 22. In this manner, waste metabolites are removed from the blood 8 at the hemodialysis module 18 and the blood 8 thus processed returns into the body by way of the heat exchanger 10.

The principal feature of the system as shown in FIG. 6 is to carry out the removal of waste metabolites and that of water from blood by the separate systems, although these operations have been simultaneously effected in conventional hemodialysis modules. To remove water from blood by conventional dialysis, a pressure is applied to the blood so that while using a dialytic membrane as an ultrafiltration membrane, water is caused to flow out from the blood to the side of a dialysate. This method cannot however be considered to be the best as a water-removing method since salts and useful constituents are also caused to flow out together with water from the blood. Hemopurification therapy, which is more efficient than that available from conventional hemodialysis, is thus feasible when the removal of water from blood is effected by the hemopurification system of this invention and that of waste metabolites is performed by hemodialysis. If water is first removed from blood by the hemopurification system of this invention and the resultant blood is thereafter subjected to hemodialysis as shown in FIG. 6, the concentrations of waste metabolites in the blood after the removal of water are hence increased, leading to accelerated removal of such waste metabolites from the blood in the hemodialysis step. Except for this advantage, effects similar to those available from the use of the combined system depicted in FIG. 6 can also be brought about even if the hemodialysis is first performed and the removal of water is then effected in accordance with this invention.

Incidentally, removal of waste metabolites, for example, urea, uric acid, creatinine, M.M. and the like from blood means to lower the concentrations of solutes in the blood. In other words, it means to lower the osmotic pressure of the blood. Namely, the osmotic pressure of the blood begins to drop concurrently with the initiation of therapy. As a result, the osmotic pressure of cell fluids in the body starts increasing relative to the osmotic pressure of the blood although both osmotic pressures has been balanced until the initiation of the therapy. Although it is also intended to remove water from the cells, the water content of the cells is conversely increased because water is caused to penetrate from the blood into the cells. To cope with this drawback, in the conventional hemodialysis the concentration of $Na^+$ ions or the like in a dialysate is increased so as to avoid the imminent drop in the osmotic pressure of blood. This approach however results in an increase of the concentration of $Na^+$ ions or the like in the blood, although such $Na^+$ ions or the like had to be removed from the blood for successful therapy. Therefore, the above method is not believed to be the most suitable therapy.

Use of the hemopurification system of this invention permits effective therapy without encountering such a problem as described above. Referring to FIG. 6 by way of example, the hemodialysis system is bypassed for a while after the initiation of hemopurification therapy. During this period of time, waste metabolites are not removed from the blood by the hemodialysis system and the removal of water from the blood is only performed in accordance with the present invention. As a result, the osmotic pressure of the blood increases and the osmotic pressure of cell fluids in the body decreases relative to the osmotic pressure of the blood. Water is hence caused to penetrate from the cell fluids into the blood, thereby making it possible to remove water from the cell fluids. Thereafter, the hemodialysis system is progressively actuated to remove waste metabolites and water from the blood and at the same time, water from the cell fluids. The degree of actuation of the hemodialysis system can be adjusted by either increasing or decreasing the flow rate of a dialysate.

Figure 7:
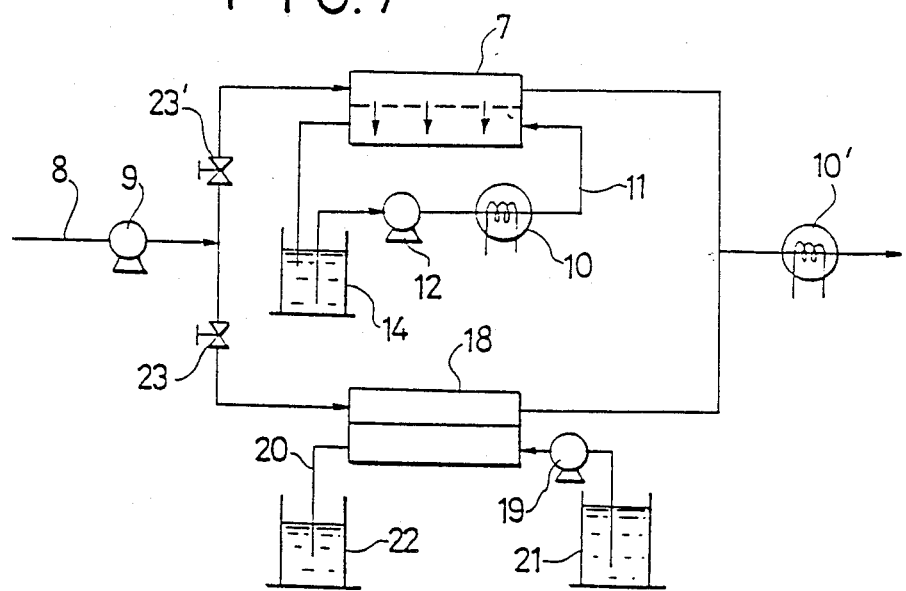

FIG. 7 illustrates another exemplary mode of operation, which enables to actuate the above-mentioned hemodialysis system more efficiently. Namely, the hemopurification system 7 and hemodialysis system 18 are connected in parallel to each other. The flow rates of blood, which flows into the respective systems, are controlled by a blood flow-rate control valve 23. The system of FIG. 7 permits full control of the osmotic pressure of the blood along the entire period of its processing so as to remove both waste metabolites and water from the blood and water from cell fluids.

In FIG. 7, elements 23 and 23' are each a valve, while elements 10 and 10' are each a heat exchanger.

Certain application examples of the apparatus of this invention will hereinafter be described to facilitate the understanding of the present invention. It should however be borne in mind that the following application examples are merely illustrative and should hence not be construed in a sense limiting the manner of use of the apparatus of this invention.

EXAMPLE 1

Figure 8:
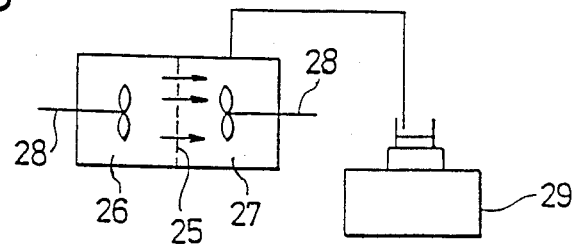
FIG. 8 schematically illustrates a hemopurification apparatus according to the first embodiment of this invention.

Water was removed from blood 26 by an apparatus shown in FIG. 8. A polytetrafluoroethylene membrane (pore size: 0.2 $\mu$m; membrane thickness: 50 $\mu$m; effective surface area: 12 cm$^2$) was used as a membrane 25, while bovine blood was used as the blood 26 subsequent to its adjustment to 20% hematocrit. A purified saline solution was used as an absorption liquid 27. While maintaining the temperature of the absorption liquid 27 constant at 16° C., the temperature of the blood was varied. Results are shown in Table 1. Sufficient performance of water removal was recognized. On the other hand, it was confirmed that no salts or any other constituents in the blood leaked into the absorption liquid. In FIG. 8, numerals 28 and 29 indicate a stirrer and electronic balance, respectively.

TABLE 1

| Temperature of blood [°C.] | Temperature of absorption liquid [°C.] | Difference in water vapor pressure $\Delta P$ [mmHg] | Flux [kg/m$^2$hr] |
| --- | --- | --- | --- |
| 24 | 16 | 8 | 3.8 |
| 28 | 16 | 14 | 6.7 |
| 34 | 16 | 20 | 9.2 |

EXAMPLE 2

Figure 9:
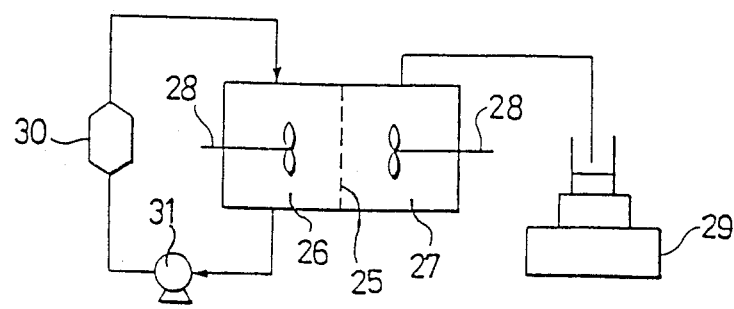
FIG. 9 schematically illustrates a hemopurification apparatus according to the second embodiment of this invention.

By an apparatus shown in FIG. 9, removal of water and adsorption of waste metabolites from blood were performed simultaneously. Results are shown in Table 2. The membrane 25 was the same type as that employed in Example 1. As an adsorbent 30 was employed granulated petroleum pitch carbon coated with nitrocellulose. Bovine blood was used as the blood 26 after its adjustment to 20% hematocrit. The temperature of the blood 26 was 34° C. Deionized water was used as the absorption liquid 27 and its temperature was maintained at 16° C. The system demonstrated the possibility of simultaneous removal of both water and water metabolites from blood. Designated at numerals 28, 29 and 31 in the drawings were a stirrer, electronic balance and blood pump, respectively.

TABLE 2

|  |  | Run 1 | Run 2 |
| --- | --- | --- | --- |
| Flow rate of blood | (ml/min) | 250 | 250 |
| Urea clearance | (ml/min) | 35 | 50 |
| Uric acid clearance | (ml/min) | 200 | 195 |
| Creatinine clearance | (ml/min) | 120 | 175 |
| M.M. clearance | (ml/min) | 100 | 135 |
| Amount of water removed | (kg/m$^2$hr) | 9.0 | 8.5 |

Having now fully described the invention, it will be apparent to one of ordinary skill in the art that many changes and modifications can be made thereto without departing from the spirit or scope of the invention as set forth herein.

What is claimed as new and is secured by Letters Patent is:

1. A hemopurification apparatus for removing water from human blood, which comprises:
   (a) means for pumping blood into one of two compartments of a hemopurificaiton module;
   (b) means for pumping an absorption fluid into the other of said two compartments of said hemopurification module;
   (c) a hemopurification module, connected to each of said pumping means, having first and second compartments, each of which is defined by a barrier means, and which are separated from each other by a porous membrane which is permeable to gas, but impermeable to liquid, wherein said first compartment receives pumped blood and said second compartment receives an absorption liquid having a vapor pressure which is lower than that of blood, whereby a portion of the water in the blood is allowed to pass as water vapor through the porous membrane; and
   (d) a heat exchanging means fluidly connected to and downstream of said first compartment of said hemopurification module for adjusting blood temperature substantially to body temperature prior to the return thereof to the human body, and a heat exchanging means fluidly connected to and upstream of said second compartment of said hemopurification module for adjusting the temperature of said absorption liquid to a temperature of about 10° to 38° C. prior to the entry thereof into said second compartment; and wherein said apparatus further comprises a hemodialysis module for removing waste metabolites from blood, fluidly connected to the first compartment of said hemopurification module, and a means for dividing the pumped blood at a predetermined flow-rate ratio into two blood streams, one of said streams being allowed to pass through the hemopurification apparatus for removing water, the other stream being allowed to pass through the hemodialysis module for removing waste metabolites, the two blood streams being combined after their respective passage.

2. A hemopurification apparatus for removing water from human blood, which comprises:
   (a) means for pumping blood into one of two compartments of a hemopurification module;
   (b) means for pumping an absorption fluid into the other of said two compartments of said hemopurification module;
   (c) a hemopurification module, connected to each of said pumping means, having first and second compartments, each of which is defined by a barrier means, and which are separated from each other by a porous membrane which is permeable to gas, but impermeable to liquid, wherein said first compartment receives pumped blood and said second compartment receives an absorption liquid having a vapor pressure which is lower than that of blood, whereby a portion of the water in the blood is allowed to pass as water vapor through the porous membrane; and (d) a heat exchanging means fluidly connected to and downstream of said first compartment of said hemopurification module for adjusting blood temperature substantially to body temperature prior to the return thereof to the human body, and a heat exchanging means fluidly connected to and upstream of said second compartment of said hemopurification module for adjusting the temperature of said absorption liquid to a temperature of about 10° to 38° C. prior to the entry thereof into said second compartment; and wherein said apparatus further comprises a hemodialysis module for removing waste metabolites from blood, fluidly connected to the first compartment of said hemopurification module, and a means for dividing the pumped blood at a predetermined flow-rate ratio into two blood streams, one of said streams being allowed to pass through the hemopurification apparatus for removing water, the other stream being allowed to pass through the hemodialysis module for removing waste metabolites, the two blood streams being combined after their respective passage, the porous membrane being a membrane containing a number of pores, the diameter of which range from 0.02–10 $\mu$m, and which membrane is made of a hydrophobic material selected from the group consisting of polytetrafluoroethylene, polypropylene and polyethylene.

* * * * *